United States Patent
Wolff et al.

(10) Patent No.: US 6,834,242 B2
(45) Date of Patent: Dec. 21, 2004

(54) PROCESS FOR ANALYZING PRESSURE VARIATION IN A PERFUSION APPARATUS COMPRISING SEVERAL UNITS

(75) Inventors: Rémi Wolff, Route de la Forteresse (FR); Jean-Claude Rondelet, Le Perrin (FR)

(73) Assignee: Fresenius Vial SAS, Brezins (FR)

( * ) Notice: Subject to any disclaimer, the term of this patent is extended or adjusted under 35 U.S.C. 154(b) by 464 days.

(21) Appl. No.: 09/809,189

(22) Filed: Mar. 16, 2001

(65) Prior Publication Data

US 2001/0023345 A1 Sep. 20, 2001

(30) Foreign Application Priority Data

Mar. 16, 2000 (FR) .............................................. 00 03509

(51) Int. Cl.[7] .............................................. G06F 15/00
(52) U.S. Cl. ............................ 702/50; 604/67; 604/155
(58) Field of Search ................................ 604/154, 155; 702/50

(56) References Cited

U.S. PATENT DOCUMENTS

| | | | |
|---|---|---|---|
| 5,304,126 A | * 4/1994 | Epstein et al. | ................. 604/67 |
| 5,464,392 A | 11/1995 | Epstein et al. | |
| 5,501,665 A | * 3/1996 | Jhuboo et al. | ................. 604/65 |
| 5,647,853 A | 7/1997 | Feldmann et al. | |

FOREIGN PATENT DOCUMENTS

| | | |
|---|---|---|
| DE | 19642234 C1 | 4/1998 |
| EP | 0960627 A2 | 12/1999 |
| FR | 2710537 A1 | 7/1997 |

* cited by examiner

*Primary Examiner*—Kamini Shah
(74) *Attorney, Agent, or Firm*—Westerman, Hattori, Daniels & Adrian LLP

(57) ABSTRACT

The invention concerns a method to analyze the pressure variation in a perfusion device including multiple perfusion modules each equipped with a pump to deliver a liquid to be perfused in a line placed downstream from the pump as well as a means to measure the pressure in the line, with junction points enabling connection of certain lines among each other or certain lines with lines from units outside the perfusion device. This process consists first in determining whether there is an acceptable explanation for a pressure variation (increase or reduction in the flow rate in a module) and whether this variation concerns modules other than that which detected it first, and which ones, to then act on the perfusion device according to the result of this analysis, either by modifying the analytical parameters in the various modules affected if the pressure variation has an acceptable explanation or by simultaneously stopping all the modules affected by this variation in flow rate and by dealing with the source of the malfunction (rupture or obstruction).

28 Claims, 4 Drawing Sheets

PROCESS FOR ANALYZING PRESSURE VARIATION IN A PERFUSION APPARATUS COMPRISING SEVERAL UNITS

FIELD OF THE INVENTION

The invention concerns a method for analysis of the pressure variation in a perfusion device including several perfusion modules each equipped with a pump to impel a liquid to be perfused in a line placed downstream from the pump as well as means for measuring the pressure in the line, with junction points enabling connection of certain lines with each other or certain lines with lines originating in units external to the perfusion device as well as a perfusion device for implementation of the process.

BACKGROUND OF THE INVENTION

Perfusion devices usually include a source of liquid connected to a flexible tube which is extended by a cannula or a catheter designed to be inserted into the patient's body. To ensure a controlled flow rate of the liquid, it is common to place a pump along the tube. This pump, when it is of the syringe type, also contains the source of liquid.

When multiple products are to be injected, it is sometimes necessary to use a plurality of these perfusion units. The lines from certain pumps may be connected to each other to allow mixing of different products. The different units are equipped with control means which can trigger alarms or even interrupt the perfusion when certain control criteria are verified.

Proper progress of the perfusion may, in certain cases, be vital. It is thus imperative that the product be administered in accordance with the intended administration plan.

However, incidents sometimes develop which disrupt the progress of the perfusion of one of the products. These incidents are of three types:

an obstruction in the line downstream from the pump;
a rupture of the line downstream or upstream from the pump, or an obstruction upstream from the pump;
a variation in the flow rate in a pump whose line is connected by a junction point with other lines (for example, in the case of a bolus).

These incidents all translate into a variation of pressure in the affected line. Thus, an increase in the pressure in the line k will be noted, for example, in the following cases:

obstruction in the line k;
increase in the flow rate, for example, within the framework of a bolus, in a line j connected to the line k by a junction point.

On the contrary, a reduction in pressure will be noted, for example, in the following cases:

rupture of the line;
reduction in the flow rate in a line j connected to the line k by a junction point.

In the prior art devices, each perfusion unit, or module, is generally equipped with means to monitor and analyze the pressure variations in order to trigger alarms and, as appropriate, to interrupt the perfusion. Thus, if the pressure measured in the line exceeds a certain value, an alarm is triggered and the pump of the affected module is stopped. The user, generally a member of the medical staff, must then determine the cause of the abnormal increase in pressure. If there is no explanation for the increase, for example, this pressure increase is not the result of a manual bolus, it must be concluded that an obstruction has occurred downstream from the pump. However, since the occurrence of the obstruction, the pump has continued to pump until the pressure in the line reaches an alarm value. If the obstruction is eliminated suddenly, all the liquid under excess pressure downstream from the pump and which should have been administered over a certain period of time is delivered abruptly. To prevent such a phenomenon, the pump affected by the obstruction is stopped, then operated in reverse to aspirate the quantity of liquid released since the formation of the obstruction, so as to completely eliminate the bolus. Only at this time can the obstruction be eliminated without danger.

This system of individual detection of pressure for each line from a pump is very effective as long as the affected line is not connected to another line. However, in multiple unit perfusion devices, it is not rare that certain lines are connected in a junction point. If an obstruction develops downstream from such a junction point, the pump whose alarm threshold is the lowest will issue an alarm signal first and will begin to pump in reverse until the disappearance of the excess pressure in its line. However, the other pumps whose lines are connected at the junction point have not yet detected any obstruction because their alarm thresholds have not yet been reached. They thus continue to pump normally, feeding the excess pressure. The pump which is in reverse operation will thus not only aspirate what it delivered after the occurrence of the obstruction, but it will also aspirate the liquid delivered by the other pumps to which it is connected by the junction point. The liquid thus contained in the pump operating in reverse becomes indeterminate and can no longer be used without risk to the patient.

The same increase in pressure which caused the stopping of the pump k may be the result not of an obstruction but rather of a temporary (case of a bolus) or lasting increase in the flow of a line j connected to the line having detected the abnormal increase in pressure. The module k and the perfusion will thus have been interrupted unnecessarily.

SUMMARY OF THE INVENTION

An object of the invention is thus to perfect a process which enables avoiding malfunctions due to the fact that certain lines may be connected to each other.

This object is accomplished by the method in accordance with the invention wherein, when a pressure variation Pk in a line k is detected, an analytical process is implemented to determine the involvement of other modules j in this pressure variation. This process enables consideration of the environment of the affected module before acting, taking into account data from either another module or external data. For this, the modules must be able to communicate either among each other or with a base unit combining all the data and retransmitting them to the modules which may be affected by the data. The analytical process is launched both in the event of increase and in the event of decrease of pressure. Its objective is to analyze the environmental situation of the module affected, in order, depending on the results provided by this analysis, either to avoid an unnecessary interruption of the perfusion if the cause of this variation is explained (variation of the flow rate in a module connected by a junction point, manual bolus at a junction point with the affected line) or to simultaneously stop all the pumps affected by an obstruction or a rupture.

In a first variant, the process includes a search for data indicating a change in the flow rate in another module j. When the flow rate in one line is modified, the affected module sends out, automatically or on demand, a message concerning the modifications made. If a module k detects a pressure variation in its line, it searches for such a message. If it finds one, it will conclude that the pressure variation has a known explanation.

In a further development of this first variant, the analytical process provides, when a message indicating a modification of the flow rate in another module j has been found, for modification of the analytical parameters of the module k for at least the time the modification of flow in the module j lasts. Thus, if the module k notes that the flow rate has been increased in a second module, it modifies its analytical parameters such that it is no longer in an alarm situation. This modification may be of short duration, for example, the duration of a bolus, or lasting, if the increase in flow rate is prolonged. This process is of interest to prevent stopping the perfusion unnecessarily.

According to a second variant, the analytical process includes comparison of the slope of the pressure curve of each line i of the system with the slope of the pressure curve of the line k to determine the lines j which are potentially connected to the line k by a junction point and which may also be affected by the pressure variation. If, in a line j, a pressure increase similar to the pressure increase in the line k is noted, it is probable that the line j is connected to the line k by a junction point. Because of load losses and different means of measurement of pressure which may be used, it is possible that the pressure variations of the lines j and the line k may not be completely identical. It is possible, for example, to establish two thresholds of tolerance which will indicate, when they are reached, that the lines are definitely connected or that they are only probably connected to each other. This information enables better assessment of the interactions of these modules among each other to more precisely analyze the pressure variations in a line k.

A third variant provides for including in the analytical process the comparison of the rate of increase of pressure in the line k with the theoretical rate it should have if an obstruction developed in the line upstream from any junction point with another line. If the module is used alone, i.e., without connection to other lines, it is possible, based on the flow rate and the compliance of its constituting elements, to determine the theoretical rate of the pressure increase in the event of an obstruction in the line. If the line k in which a pressure increase has been detected is connected to other lines, the rate of the pressure increase in the module k will not correspond to the theoretical rate calculated for the same module considered in isolation. In contrast, if this rate is similar to the theoretical rate, it is very likely that the obstruction is located upstream from any junction point.

These three variant embodiments of the analytical process permit, on the one hand, to search for an admissible explanation for a pressure variation and, on the other, to determine whether the module in which the pressure variation has been detected is connected to other modules, and if so, what these modules are. However, these embodiments provide only initial information, which is sometimes inadequate. It is thus preferable to combine these variants in order to refine the analysis.

Thus, in a subvariant combining the second and the third variants, the analytical process includes the calculation of the theoretical rate of the pressure increase which should be observed in the line k in the event of obstruction downstream from junction points with the lines j and the comparison of the actual rate of increase in the line k with this theoretical rate. If the process according to the third variant reveals that the module cannot be considered to be isolated (consequently, that there is no obstruction upstream of any junction point with other modules), the process according to the second variant is implemented to determine what modules are affected by this pressure variation, i.e., those which are connected to the line k by a junction point. When it is known which other modules are affected, the theoretical rate of pressure increase in the line k if an obstruction was located downstream from the junction point of these modules is calculated using their respective flow rates and compliance parameters. If the actual rate corresponds to this new theoretical rate, it can be concluded that an obstruction has developed downstream from the junction point. Otherwise, it must be concluded that the pressure variation is probably due to a flow rate variation in a module connected to the module k or to a manual bolus at a junction point located on the line k. This hypothesis can be verified, for example, by performing the process according to the first variant.

From a practical standpoint, it is preferable to measure the pressure P1 in each line i at regular intervals and to store these measurements in a history file no later than the time when a pressure variation is detected in a line k. For certain applications, it is preferable to begin storage of the values as of the start of the perfusion in order to be able to determine, if an obstruction has developed, the instant when it occurred. It is not absolutely necessary to save the records during the entire period of the perfusion. For reasons of economy of memory, it may be preferable to store the data for only a certain period of time. This period of time will be determined based on the flow rate of the different pumps and thus on the time necessary to detect an obstruction.

Initiation of the analytical process when the pressure Pk in a line k reaches a threshold value established for each pump is within the scope of the invention. In practice, a lower threshold and upper threshold will be established for each module, with the normal pressure being between these two values. As soon as the pressure moves outside this tolerance range, the analytical process is initiated. It is possible to establish a second pair of threshold values included in the preceding range, which initiates an observation process, for example, recording the values measured.

When the results of the analytical process reveal that the pressure variation is due either to a rupture in the line (pressure reduction in one or a plurality of lines) or to an obstruction in a line (unexplained pressure increase in one or a plurality of lines), it is necessary to act as quickly as possible. That is why the method provides, when the results of the analytical process lead to the conclusion that a rupture or an obstruction has developed downstream from pump k, to stop the pump k and, as appropriate, the pumps j connected to the pump k by their respective lines at junction points located upstream from the rupture or the obstruction. Thus, not only the pump k which triggered the alarm is stopped, but so are the pumps j connected to the pump k by a junction point located upstream from the obstruction or the rupture. In the event of an obstruction, increasing the overpressure upstream from the obstruction by allowing each pump j to pump until its alarm threshold value is in turn reached is prevented. In addition, if the other modules k are not stopped, the liquids supplied by these modules will have a tendency to flow back into the line k under the effect of the pressure, resulting in an indeterminate mixture. This disadvantage is prevented by simultaneously stopping all the modules located upstream from the obstruction.

To avoid the bolus phenomenon when the obstruction is eliminated, it is in accordance with the invention to operate each pump j which was stopped for a period of time $\Delta t_j$ in reverse, at a reverse flow rate RQj proportional to the initial flow rate Qj at the time of normal operation. For this, the pumps which had the highest pumping flow rate Qs among the pumps j affected by the obstruction is determined, for example; this pump s is then run in reverse at a reverse flow rate RQs and the other pumps j at the respective reverse flow rate $$RQj=(Qj/Qs) \times RQs$$

The period of time $\Delta tj$ will be selected such that a bolus is avoided, on the one hand, and there is no aspiration of blood, on the other.

In a first variant embodiment of this process, the periods of time $\Delta tj$ during which the pumps affected by the obstruction operate in reverse at the reverse flow rate RQj are selected identical for all said pumps and equal $$\Delta t=(T2-T0) \times \Sigma(Qj)/\Sigma(RQj),$$

where T0 is the time at which the obstruction occurred, this time T0 being determined by means of the history of measurements recorded from the beginning of the perfusion, and T2 is the time at which the obstruction was detected. To apply this variant, it is thus necessary to begin the recording of data concerning the pressure measurements from the beginning of the perfusion and it is necessary to save them long enough to be able to determine the time T0 at which the obstruction developed.

In a second variant embodiment of this process, each pump j affected by the obstruction operates in reverse until the pressure determined in its line has dropped below an established threshold Plj. For this variant embodiment, it is thus unnecessary to determine in advance a specific period of time $\Delta tj$, the monitoring of the pressure in each tube j being adequate to stop the affected pumps.

To facilitate the work of the medical staff, the result of the analytical process is displayed in the form of a diagram combining the various lines, for example, on a screen integrated with the base unit.

The object of the invention is also accomplished in that the multiple pump perfusion device is equipped with a device to implement the method according to the invention. This device to implement the method can be placed either directly on each pump if the pumps are capable of communicating with each other, or in an external control device connected to each pump, such as a computer or a base unit.

BRIEF DESCRIPTION OF THE DRAWINGS

Exemplary embodiments of the invention are described in the following with reference to the annexed figures and schematic diagrams.

DESCRIPTION OF PARTICULAR EMBODIMENTS

Figure 1:
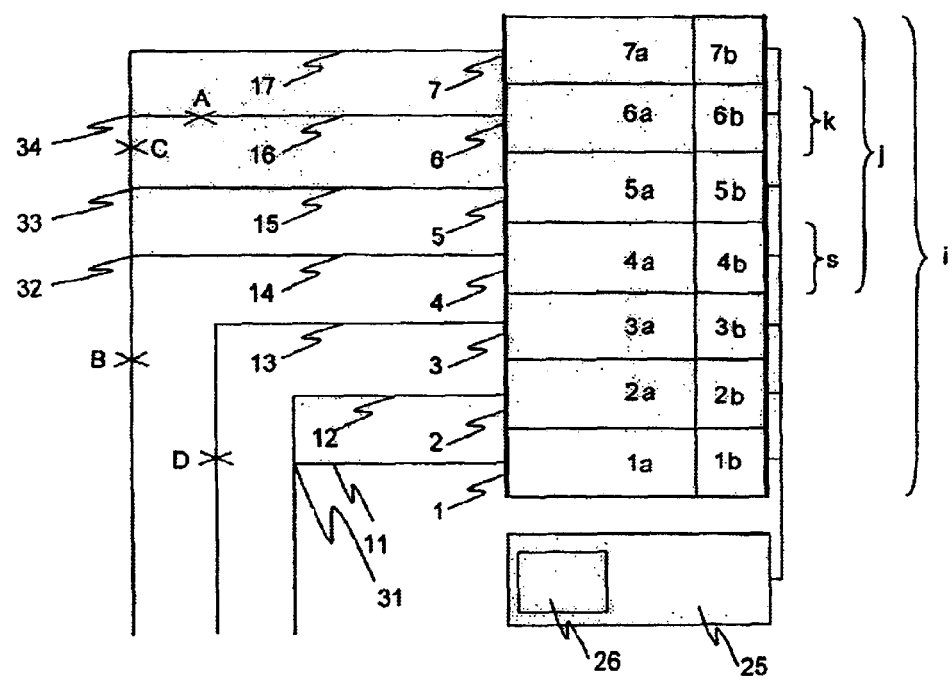
FIG. 1 depicts a perfusion device with seven modules, some of which are connected by junction points.

A perfusion device to which the method constituting an object of the invention may be applied includes multiple modules (1 to 7). Each of these modules (1 to 7) has a pump (1a to 7a) delivering a liquid to be perfused in a line (11 to 17) and a pressure sensor (1b to 7b) indicating the pressure in the corresponding line. The pumps may be either volume dosing pumps, in which case they are supplied by an external source of liquid, or pumps of the syringe type, in which case the source of liquid is the syringe itself. The pressure detectors can be placed downstream from the pump; this will generally be the case for dosing pumps. For the syringes, the detectors can be placed on the element actuating the syringe. Junction points (31, 32, 33, 34) enable connection of certain lines among each other. The modules are connected to a base unit (25) which centralizes the data from and to the various modules. It is also capable of managing data from the outside. Instead of using a base unit, it is also possible for each module to be able to communicate directly with the other modules.

Before starting perfusion, certain parameters are established for each module, depending on the product which it must deliver. The following are thus established for each module i:

the flow rate Qi;

the analytical parameters of each module i, i.e., the upper pressure limits P1i and P2i and the lower pressure limits P3i and P4i; the parameters P1i and P3i define the normal range of pressure variation and the parameters P2i and the P4i, the values which trigger an action when they are reached; the limit pressures PLi which must not in any case be exceeded (it is possible, for example, to establish PLi=P2i).

For the sake of simplicity, the following legend will be used i for the parameters which are to apply to all the pumps;

j for the parameters which refer only to the pumps affected by an obstruction;

k for the parameters referring to the pump which detected a pressure variation;

s for the parameters referring to the pump with the highest flow rate Qj among the pumps j affected by an obstruction.

This legend is illustrated in FIG. 1. The obstruction developed at B; the module (6) detected a pressure variation; the module (4) is, among the modules j (4 through 7) affected by the obstruction, the one whose flow rate Qs is the highest.

The perfusion is started and the pressure in the lines i (11 through 17) is measured, every 10 seconds, for example. These values are preferably recorded in order to have a history of pressure in the event of a pressure variation.

The values of the pressure Pi measured in each line i (11 through 17) are immediately compared to the corresponding threshold values P1i and P3i. As soon as the value Pk in a line k (for example, 6) reaches one of the two threshold values P1k or P3k, indicating that the pressure is outside the normal range, the analytical process is initiated. The time when the pressure Pk has reached or exceeded one of these threshold values P1k or P3k is labeled T1.

In the case of the first variant, the analytical process searches for a message from one of the other modules indicating that the flow rate in that module has been modified and which could explain this pressure deviation. Such data may come directly from the module, if the modifications were made on the module, or from the base unit, if the modifications were made through its intervention. The message may be sent preventively to all the modules, or only searched for as needed by the module whose pressure has left the normal range or by the base unit if it is responsible for the analysis.

When such a message is found, the parameters of the module whose pressure has left the normal range are changed to take into account this change in flow rate and the resultant pressure change. If, for example, the message indicates that the flow rate of one of the modules of the perfusion device was reduced and that the pressure Pk of the module k has dropped below the limit P4k, this limit P4k at least is revised downward. Likewise, if the message indicates an increase of the flow rate in a module j, the parameter P2k at least is revised upward. The new parameters P2k and P4k must, however, be changed again when the flow rate in the module j is changed again. For example, if a bolus is effected in the module j, the modification of the flow rate is only temporary. Consequently, the limit P2k is increased (for example, up to the limit value PLk for this module) for the period of the bolus before being returned to its initial value at the end of the bolus.

Figure 2:
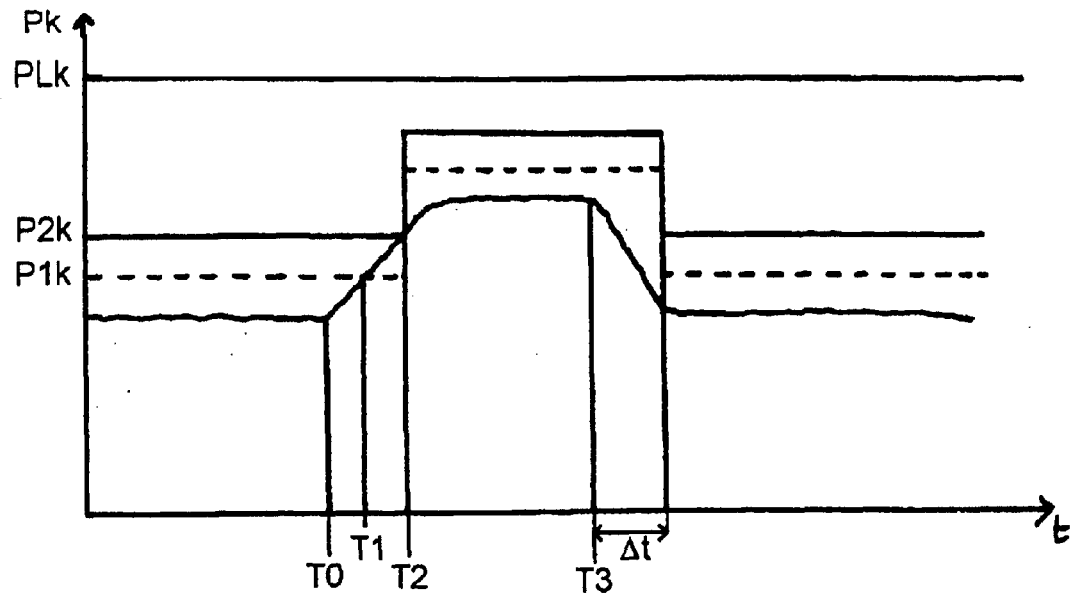
FIG. 2 depicts a pressure curve in the module k during an increase in the flow rate in a connected module j.

FIG. 2 depicts an example of a pressure curve in the case of a flow rate increase. The modules j and k are connected by a junction point (for example, the modules (1) and (2)). A decision is made to increase the flow rate of the substance administered by the module j. At this point in time T0, the limit value P2j is increased so that the module j will not generate an alarm. The pressure increases in the line j as well as in the line k which is connected thereto. At the time T1, a little after T0, the pressure in the module k reaches the established limit P1k and at the time T2, the pressure Pk exceeds the threshold value P2k, triggering the start of the analytical process. Having found a message from the module j indicating that the flow rate in the module j was increased, the parameter P2k is increased as is the parameter P1k in order to take into account the new flow rate in the module j. When the flow rate in the module j is returned to its initial value, at time T3, the pressure begins to drop, but is not reduced immediately. Consequently, the values P1k and P2k are not returned to their initial values until after a period of time $\Delta t$.

Figure 4:
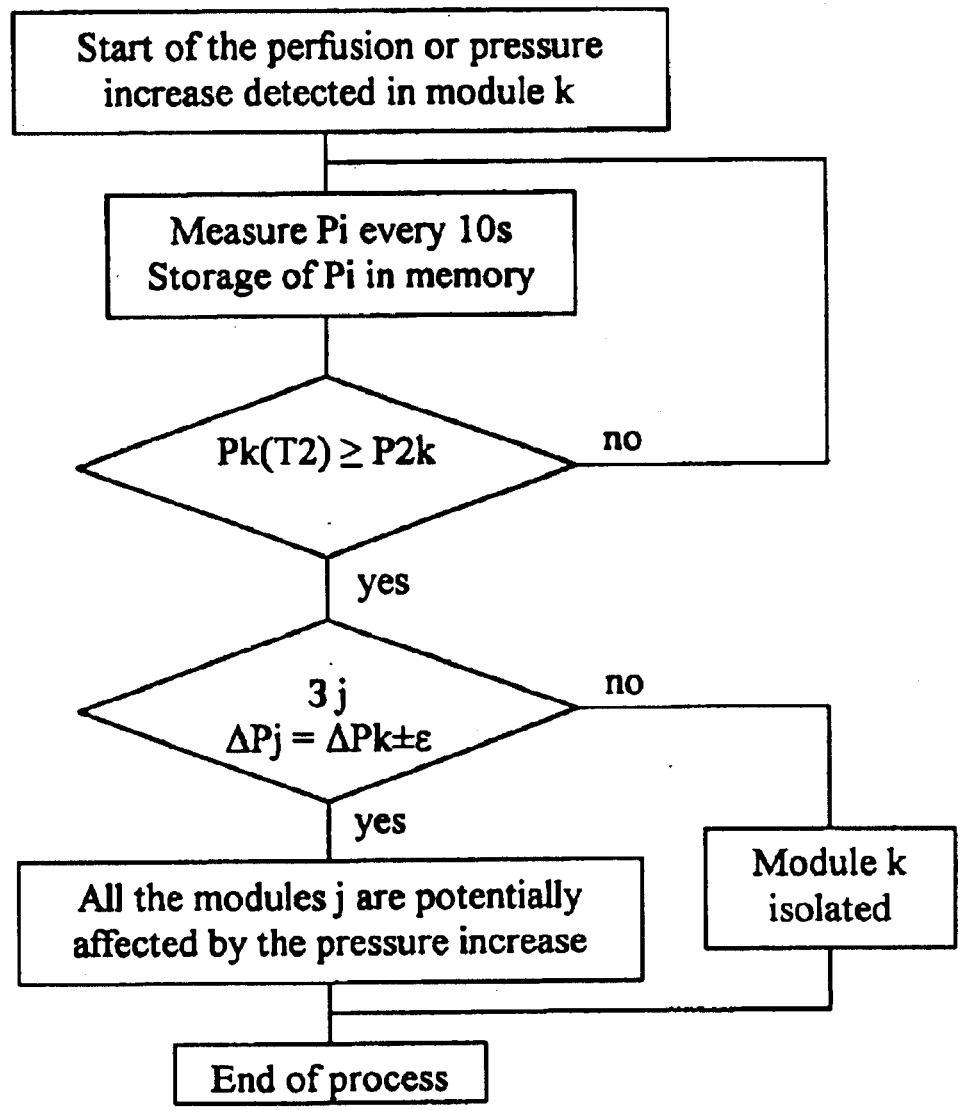
FIG. 4 is a schematic diagram of a third variant embodiment of the analytical process.

In the second variant of the analytical process, the search is performed primarily to determine the modules affected by the pressure variation detected in the module k. In contrast to the first variant, data which may explain the pressure variation are not taken into account. The schematic of this variant is depicted in FIG. 4.

When, in a module k, the pressure Pk exceeds the value P1k at a time T1, all the values Pi measured starting from this time T1 are recorded (unless, preventively, the values Pi since the beginning of the perfusion have been systematically recorded). When the pressure Pk exceeds the second threshold value P2k, the pressure difference between the time T1 and the time T2 is calculated for each module i:

$$\Delta Pi = Pi(T2) - 2Pi(T1) \quad [1]$$

The $\Delta Pi$ values thus obtained are then compared to $\Delta Pk$. Theoretically, all the lines connected to the line k by a junction point should see their pressure vary in the same manner as the line k. In practice, this pressure variation is not absolutely identical, especially because of the differences in compliance of the various modules and of the pressure measurement means. Thus, two tolerance ranges characterized by $\epsilon 1$ and $\epsilon 2$, with $\epsilon 1 < \epsilon 2$, are established. When the following equation is verified:

$$\Delta Pj = \Delta Pk \pm \epsilon 1 \quad [2]$$

it is possible to conclude that the line j is very likely connected to the line k by a junction point.

If, in contrast, the equation [2] is not verified, but the following equation is verified:

$$\Delta Pj = \Delta Pk \pm \epsilon 2 \quad [3]$$

it is possible to conclude that the line j is probably connected to the line k by a junction point.

If even the equation [3] is not verified, the line j is very likely not connected to the line k. For example, $\epsilon 1 = 30\%$ and $\epsilon 2 = 50\%$ are established.

This second variant of the analytical process thus makes it possible to distinguish the lines j affected by the pressure variation detected by k from the other lines i of the perfusion device which are not.

If, for example, the presence of an obstruction is detected in the line k, it is possible then to conclude that this obstruction affects not only the module and the line k, but also the modules and the lines j, whereas the other modules are not affected.

Referring again to the example depicted in FIG. 1, if an obstruction develops in C and the pressure in the line (7) exceeds the threshold P1(7) then P2(7), the analysis according to the second variant should show that the pressure in the line (6) has increased comparably between the time T1 and the time T2, whereas the pressure in the other lines (1 through 5) has remained stable or at least has not varied similarly. If, in contrast, a rupture develops in B and the pressure P(7) goes below the threshold value P3(7) then P4(7), the analysis according to this second variant should show that the pressure in the lines (4 through 6) has also dropped comparably. This process is thus usable both for a pressure increase and for a reduction. It is not necessary that the pressure variation be due to an obstruction or a rupture in a line: this process can also be used when the pressure variation in the line k is due to a variation of the flow rate in a line j connected to the line k by a junction point.

It is also possible, if the pressures are recorded from the beginning of the perfusion in a history file, to not trigger the process until the time that Pk leaves the range [P4k:P2k] and to subsequently calculate the slope of the curve by using the data of the history file. If, for example, Pk exceeds the alarm threshold P2k at the time T2, the history is searched for the time Pk passed a certain threshold, for example, P1k, and the slope of the pressure curves of all the lines between this time and T2. If, on the other hand, for economic reasons, is preferred to record the pressure values only in the event of malfunction, it would then be necessary to initiate the process according to the second variant as soon as pressure Pk leaves the normal pressure range [P3k:P2k].

Figure 3:
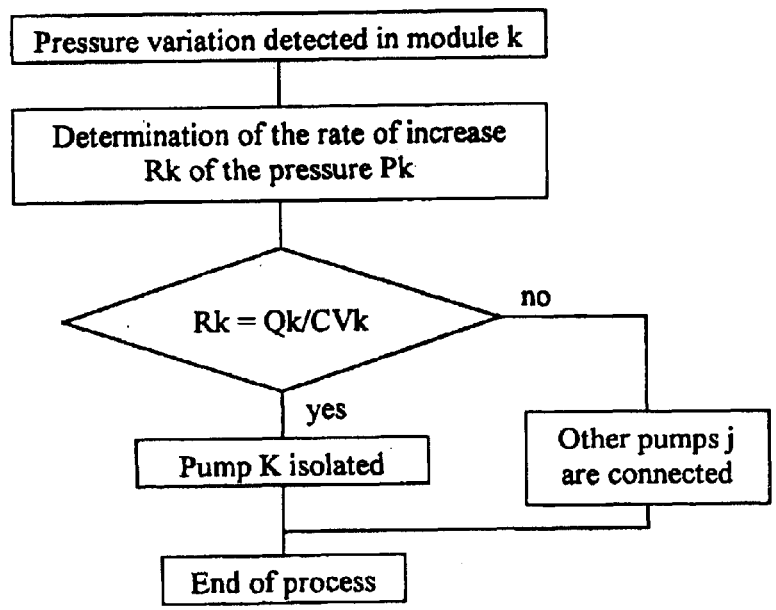
FIG. 3 is a schematic diagram of a second variant embodiment of the analytical process.

The third variant of the analytical process consists primarily in determining whether the pressure variation detected in a line k is comparable to that which it would have if the line was considered in isolation in an obstruction situation. For this, the rate of increase of the pressure is compared. The schematic diagram of this variant is depicted in FIG. 3.

When an obstruction develops in the line k, the pressure Pk increases at the rate Rk depending on the flow rate Qk of the pump k and its compliance volume CVk. This compliance volume is a virtual volume due to the elasticity of the system when the pressure is greater than normal pressure. In a syringe-type pump, for example, this compliance volume is due primarily to the stopper. It is calculated using a coefficient of compliance volume CVCk as a function of the pressure Pk:

$$CVk = CVCk \times Pk \quad [4]$$

By definition, $$Pk(t) = Rk \times t \quad [5]$$

and $$CVk = Q \times t \quad [6]$$

Consequently, if the obstruction affects only the pump k (for example, an obstruction in A or in D), the rate of pressure increase downstream from the pump k will be due only to the contribution of the pump k and it will equal:

$$Rk = Qk/CVCk \quad [7]$$

On the other hand, if the obstruction affects pumps other than the pump k (for example, if the obstruction develops in B or in C), the rate of pressure increase downstream from the pump k will depend on the rate of flow of the other pumps j and of their respective coefficients of compliance volumes. It will thus equal:

$$Rk = \Sigma Qj/\Sigma CVCj \quad [8]$$

Consequently, if the rate of the pressure increase is compared to that which should be obtained if the pump was considered in isolation (Equation [7]), it will be possible to determine whether other pumps j are affected by the obstruction.

These process variants are based on different principles. The first variant makes it possible to find, within the perfusion device, an explanation of a pressure variation in one of the modules. This second variant makes it possible to determine if modules are connected to each other. The third variant makes it possible to determine whether an obstruction has occurred and whether it affects one or a plurality of lines. It is thus of interest to combine these different variants to obtain a more refined analysis of the situation.

This process combining these different process variants should make it possible to determine whether there is an acceptable explanation for a pressure variation (increase or reduction in flow rate in a module), whether this variation affects modules other than that which detected it first and if so, which ones to then act on the system according to the result of this analysis either by modifying the analytical parameters in the various modules affected if the variation in flow rate has an acceptable explanation, or to stop all the modules affected by this variation in flow rate and remedy the source of the malfunction.

When a pressure variation is detected in the line k, i.e., when Pk leaves the normal range [P3k:P1k], the third variant of the process is implemented first. If it leads to the conclusion that the rate of pressure increase is similar to that which would be measured in the line if it were isolated, it is possible to conclude that an obstruction has developed in the line k upstream from any junction point with other lines (for example, on A or on D). This conclusion would, however, be incorrect if, exceptionally, the line k was connected to other lines j of which the flow rates and the respective coefficients of compliance volume were similar to those of the module k.

The analysis continues by determining which modules j are affected by this pressure variation, using the analytical process according to the second variant.

If, as indicated by the first part of the analysis, only the module k is affected, no other module should present a pressure variation similar to that detected in the module k. If the situation is the exceptional situation mentioned above, this second part of the analysis enables its detection.

As soon as the modules j affected or potentially affected by this pressure variation are known, the theoretical rate of pressure increase in the line k is recalculated starting from the hypothesis that an obstruction has developed downstream from the junction points of lines affected or potentially affected and taking into account the flow rates and the respective coefficients of compliance volume of these modules j. Then, the rate of the pressure increase in the line k is compared again with this new theoretical rate. If the comparison is positive, it is very likely that an obstruction has developed downstream from the junction points of these lines j. Otherwise, the pressure increase is probably due to another cause, for example, a bolus in one of the lines j. This hypothesis is verified by researching according to the first variant of the process whether there is an explanation for this pressure variation.

The order of the process variants is not significant. It is possible, of course, to begin by seeking an admissible explanation, verifying that the module in which the flow rate has been changed is in fact connected to the module k, changing the analytical parameters of the module k, accordingly, as well as those of the modules which are also connected to the module k. If no explanation is found, it is then necessary to search the other modules j affected by the pressure variation and see whether there is an obstruction or rupture in a common line in order to stop all the modules and, if appropriate, put these modules into reverse operation. It is then possible to further refine the results by applying coefficients of fuzzy logic to these different variants.

Once the analytical process has enabled determination of the exact situation in the perfusion device, it is necessary to act appropriately.

In the conventional devices, a pressure variation outside the tolerance range in a module k leads invariably to an alarm and to stopping the pump which is in the alarm situation. The other modules, including those which are connected to the module k, continue to pump until reaching their respective alarm thresholds. The mixture from the various lines j will flow back under the effect of the pressure in the line k before the other modules j are stopped.

By using the process according to the invention, it will be determined which modules are affected by the pressure variation and an explanation for this pressure variation will be sought. If an explanation is found, the control parameters (P1j, P2j, P3j, and P4j) of the modules j affected by the pressure variation will be modified for as long as the modification which caused the pressure variation lasts. The modules j affected will thus not be stopped unnecessarily. If no explanation is found, it will be concluded that an obstruction or a rupture has occurred downstream from all the lines j affected by the pressure variation but upstream from the others.

Once the analysis has enabled determination, on the one hand, that the pressure variation has no explanation and, on the other, which modules are affected, it is possible to act simultaneously at the level of all the modules j affected.

If the pressure variation results from a rupture, all the modules upstream from the rupture are stopped and the rupture repaired before the perfusion is started again.

If the pressure variation results from an obstruction, all the modules located upstream from the obstruction are stopped simultaneously. Thus, reflux of an unknown mixture into the line k is avoided.

To avoid a bolus, it is necessary to return the pressure inside the lines j affected to a normal value. It is thus necessary, as in the devices with a single pump, to reverse the operation of the pump to eliminate the quantity of product delivered since the occurrence of the obstruction. In order to ensure homogeneous recovery of the liquids delivered, each pump j affected by the obstruction is reversed to a reverse flow rate RQj proportional to the initial flow rate Qj. The pump s which had the highest flow rate Qj is determined from among the pumps j. It is put in reverse operation at a reverse flow rate RQs, for example, the maximum reverse flow rate, and the other pumps j are operated in reverse with the reverse flow rate $RQj=RQs\times Qj/Qs$.

The end of the reverse pumping operation may be determined in various ways.

Figure 5:
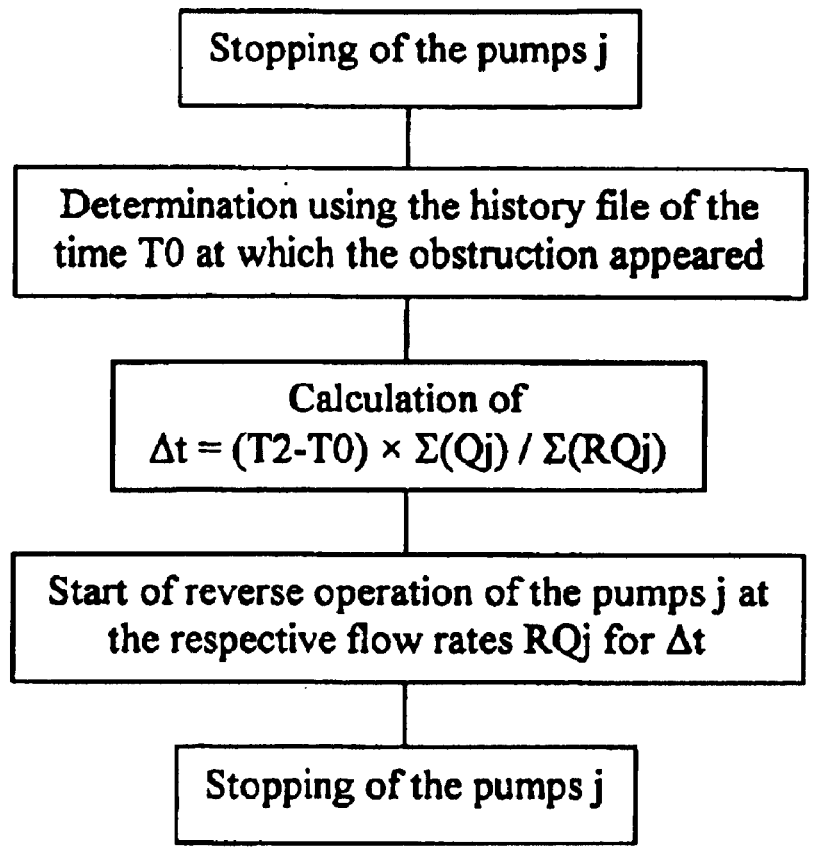
FIG. 5 is a schematic diagram of a first process of pumping in reverse of the pumps affected by the obstruction.

The first consists in initially determining the time T0 at which the obstruction developed by using the data stored in the history file. The schematic of this solution is depicted in FIG. 5. For this, it is necessary that the history file go back adequately far. T0 corresponds to the intersection of the curve of the pressure increase with the curve of the initial stable pressures. The pumps j will thus operate in reverse for a period $$\Delta t=(T2-T0)\times\Sigma(Qj)/\Sigma(RQj)=(T2-T0)\times Qs/RQs \qquad [9]$$

Figure 6:
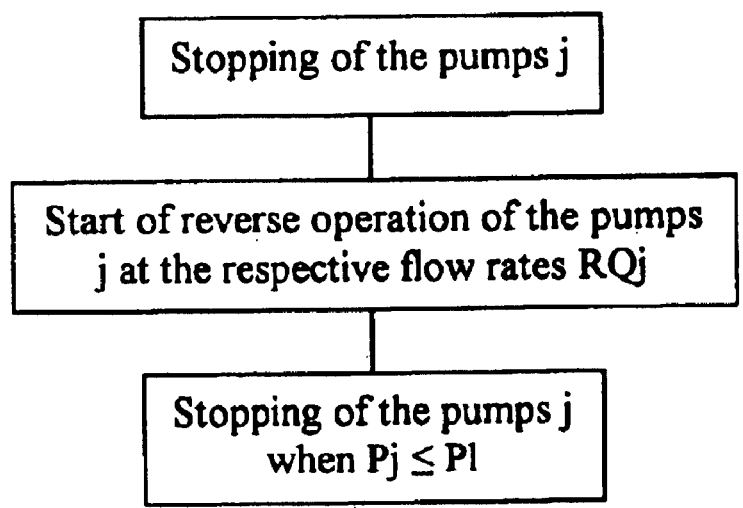
FIG. 6 is a schematic diagram of a second process variant of pumping in reverse of the pumps affected by the obstruction.

Another solution consists simply in making the pumps j pump at the flow rates RQj indicated above until the pressure Pj measured in the tubes j drops back below a threshold value P1. The schematic is presented in FIG. 6.

When the excess pressure is eliminated, the obstruction can be eliminated without danger and the perfusion device can be put back in operation.

To implement the device, it is possible to provide for connecting the control device of each pump to a computer which will manage the various control operations.

It is also possible to display, on a screen (26) placed on the base unit (25), the result of the analysis in the form of a connection diagram of the various lines. The medical staff can thus more readily find the location of the malfunction.

The method according to the invention thus enables analysis of the situation of the entire perfusion device. It is thus possible to avoid false alarms by modifying the analytical parameters if an acceptable explanation is found, or, conversely, to act directly on the group of modules affected by the malfunction detected.

What is claimed is:

1. Method for analysis of the pressure variation in a perfusion device,
    said perfusion device comprising a plurality of perfusion modules i each equipped with a pump to deliver a liquid to be perfused in a line i placed downstream from the pump as well as with means for measuring the pressure in the line i,
    at least one junction point enabling connection of at least one of the lines i with (a) at least another of the lines i or (b) at least one line from at least one unit external to the perfusion device,
    wherein said method comprises:
    detecting, among lines i of modules i, a variation of pressure Pk in a line k of a module k, and
    determining, among modules i other than module k, an involvement of one or several modules j in this pressure variation, by an analytical process.

2. Method according to claim 1, wherein the analytical process includes a search for data indicating a modification of flow rate in a module j.

3. Method according to claim 2, wherein when a message indicating a modification of flow rate in a module j has been found, parameters for analysis of the module k are modified at least as long as the modification of the flow rate in the module j lasts.

4. Method according to claim 1, wherein the analytical process includes a comparison of a slope of a pressure curve of each line i with a slope of a pressure curve of the line k to determine lines j which are potentially connected to the line k by a junction point and which may also be affected by a pressure variation.

5. Method according to claim 2, wherein the analytical process includes a comparison of a slope of a pressure curve of each line i with a slope of a pressure curve of the line k to determine lines j which are potentially connected to the line k by a junction point and which may also be affected by a pressure variation.

6. Method according to claim 3, wherein the analytical process includes a comparison of a slope of a pressure curve of each line i with a slope of a pressure curve of the line k to determine lines j which are potentially connected to the line k by a junction point and which may also be affected by a pressure variation.

7. Method according to claim 1, wherein the analytical process includes a comparison of a rate of pressure increase in the line k with a theoretical rate that it should have if an obstruction developed in the line k upstream from any junction point with another line i.

8. Method according to claim 2, wherein the analytical process includes a comparison of a rate of pressure increase in the line k with a theoretical rate that it should have if an obstruction developed in the line upstream from any junction point with another line i.

9. Method according to claim 3, wherein the analytical process includes a comparison of a rate of pressure increase in the line k with a theoretical rate that it should have if an obstruction developed in the line upstream from any junction point with another line i.

10. Method according to claim 4, wherein the analytical process includes a comparison of a rate of pressure increase in the line k with a theoretical rate that it should have if an obstruction developed in the line upstream from any junction point with another line i.

11. Method according to claim 5, wherein the analytical process includes a comparison of a rate of pressure increase in the line k with a theoretical rate that it should have if an obstruction developed in the line upstream from any junction point with another line i.

12. Method according to claim 6, wherein the analytical process includes a comparison of a rate of pressure increase in the line k with a theoretical rate that it should have if an obstruction developed in the line upstream from any junction point with another line i.

13. Method according to claim 10, wherein the analytical process includes a calculation of a theoretical rate of pressure increase which should be observed in the line k in the event of an obstruction downstream from junction points with the lines j and a comparison of the rate of pressure increase in the line k with this theoretical rate.

14. Method according to claim 11, wherein the analytical process includes a calculation of a theoretical rate of pressure increase which should be observed in the line k in the event of an obstruction downstream from junction points with the lines j and a comparison of the rate of pressure increase in the line k with this theoretical rate.

15. Method according to claim 12, wherein the analytical process includes a calculation of a theoretical rate of pressure increase which should be observed in the line k in the event of an obstruction downstream from junction points with the lines j and a comparison of the rate of pressure increase in the line k with this theoretical rate.

16. Method according to claim 1, wherein a pressure Pi in each line i is measured at regular intervals, and measurements are stored in a history file starting at the latest at a time when a pressure variation is detected in a the line k.

17. Method according to claim 1, wherein the analytical process is initiated when a pressure Pk in a the line k reaches a threshold value established for each pump.

18. Method according to claim 7, wherein when the results of the analytical process lead to a conclusion that a rupture or an obstruction has developed downstream from a pump k, the pump k is stopped.

19. Method according to claim 18, wherein pumps j connected to the pump k by their respective lines at junction points located upstream from a rupture or the obstruction are also stopped.

20. Method according to claim 18, wherein, when an obstruction is detected, each pump j which has been stopped is operated in reverse for a period of time $\Delta tj$, at a reverse flow rate RQj proportional to the initial flow rate Qj at a time of normal operation.

21. Method according to claim 20, wherein the periods of time $\Delta tj$ during which the pumps affected by the obstruction operate in reverse at the reverse flow rate RQJ are selected identical for all said pumps and equal $$\Delta t = (T2-T0) \times \Sigma(Qj)/\Sigma(RQJ),$$

where T0 is a time at which the obstruction occurred, this time T0 being determined by means of a history of measurements recorded from a beginning of the perfusion, and T2 is a time at which the pump k and possibly the pumps j were stopped.

22. Method according to claim 20, wherein each pump j affected operates in reverse until a pressure determined on its line j has dropped below an established threshold Plj.

23. Method according to claim 1, wherein a result of the analytical process is displayed in form of a connection diagram of the various lines.

24. Perfusion device comprising:

a plurality of perfusion modules i each equipped with a pump to deliver a liquid to be perfused in a line i placed downstream from the pump as well as means for measuring the pressure in the line i, at least one junction point enabling connection of at least one of the lines i with (a) at least another of the lines i or (b) at least one line from at least one unit external to the perfusion device, the modules i being capable of exchanging data among each other or with a base unit, and means for analyzing the pressure variation in the perfusion device by detecting, among lines i of modules i, a variation of pressure Pk in a line k of a module k, and determining, among modules i other than module k, an involvement of one or several modules j in this pressure variation, using an analytical process.

25. Method according to claim 1, comprising determining by the analytical process at least one of the following: (a) whether the pressure variation in line k of module k is explained in another module, (b) whether line k of module k is connected to other lines, (c) whether an obstruction has occurred and whether it affects one or a plurality of lines.

26. Method according to claim 1, further comprising acting on the perfusion device by (a) modifying analytical parameters of modules j affected by the pressure variation in line k of module k, or (b) stopping all of the modules j.

27. Device according to claim 24, wherein the analyzing means determines by the analytical process at least one of the following: (a) whether the pressure variation in line k of module k is explained in another module, (b) whether line k of module k is connected to other lines, (c) whether an obstruction has occurred and whether it affects one or a plurality of lines.

28. Device according to claim 24, further comprising means for acting on the perfusion device by (a) modifying analytical parameters of modules j affected by the pressure variation in line k of module k, or (b) stopping all of the modules j.

* * * * *